United States Patent [19]

Allen et al.

[11] 4,215,508

[45] Aug. 5, 1980

[54] APPARATUS AND METHOD FOR FUMIGATING STORED AGRICULTURAL COMMODITIES

[75] Inventors: James R. Allen, Salina, Kans.; Wolfgang F. Friemel, Heppenheim, Fed. Rep. of Germany

[73] Assignee: Research Products Company, Salina, Kans.

[21] Appl. No.: 946,766

[22] Filed: Sep. 28, 1978

[30] Foreign Application Priority Data

Jun. 22, 1978 [DE] Fed. Rep. of Germany ... 7818669[U]

[51] Int. Cl.² ............................................. A01M 13/00
[52] U.S. Cl. ........................................ 43/125; 43/131; 206/0.5; 206/820
[58] Field of Search ................... 206/820, 0.5; 43/125, 43/131; 93/DIG. 1

[56] References Cited

U.S. PATENT DOCUMENTS

| | | | |
|---|---|---|---|
| 1,005,180 | 10/1911 | Ellis | 43/131 UX |
| 2,326,931 | 8/1943 | Dalton | 93/DIG. 1 |
| 3,160,273 | 12/1964 | Reuther | 206/820 |
| 3,605,321 | 9/1971 | Lazarus | 43/131 |
| 4,101,711 | 7/1978 | Stillman | 206/819 |

FOREIGN PATENT DOCUMENTS

1411599 11/1972 Fed. Rep. of Germany .

Primary Examiner—Harold D. Whitehead

Attorney, Agent, or Firm—Fishburn, Gold & Litman

[57] ABSTRACT

An apparatus and method for fumigating stored agricultural commodities such as grain and the like, includes an applicator for porous envelopes or sachets of prepackaged pesticides of the type which react with moisture in the air and produce a toxic gas. The applicator comprises an elongate strip constructed of a flexible, porous, non-hygroscopic material. The strip has two plies which are arranged in an overlying relationship and are interconnected along a side edge thereof, and includes a plurality of seams which extend laterally across the strip and regularly interconnect the plies, and form pockets shaped for receiving the prepackaged pesticide sachets therein. The seams form a flexible hinge between adjacent pockets and interconnect the same to facilitate folding. A sachet is inserted into each pocket, the pocket is closed, and the filled applicator is deployed onto the free surface of an aggregation of stored commodity and arranged in a flat and fully extended position thereover. Water vapor in the air infiltrates the applicator and sachets and reacts with the pesticide to form a gas which permeates the commodity storage and fumigates the same. After the sachets have completely degassed, and the grain depository is vented, a free end of the applicator is grasped, and the same is longitudinally rolled or folded accordian-style along the seams, thereby quickly retreiving each of the gassed sachets, without adulterating the commodity with pesticide residue.

15 Claims, 6 Drawing Figures

U.S. Patent  Aug. 5, 1980  4,215,508
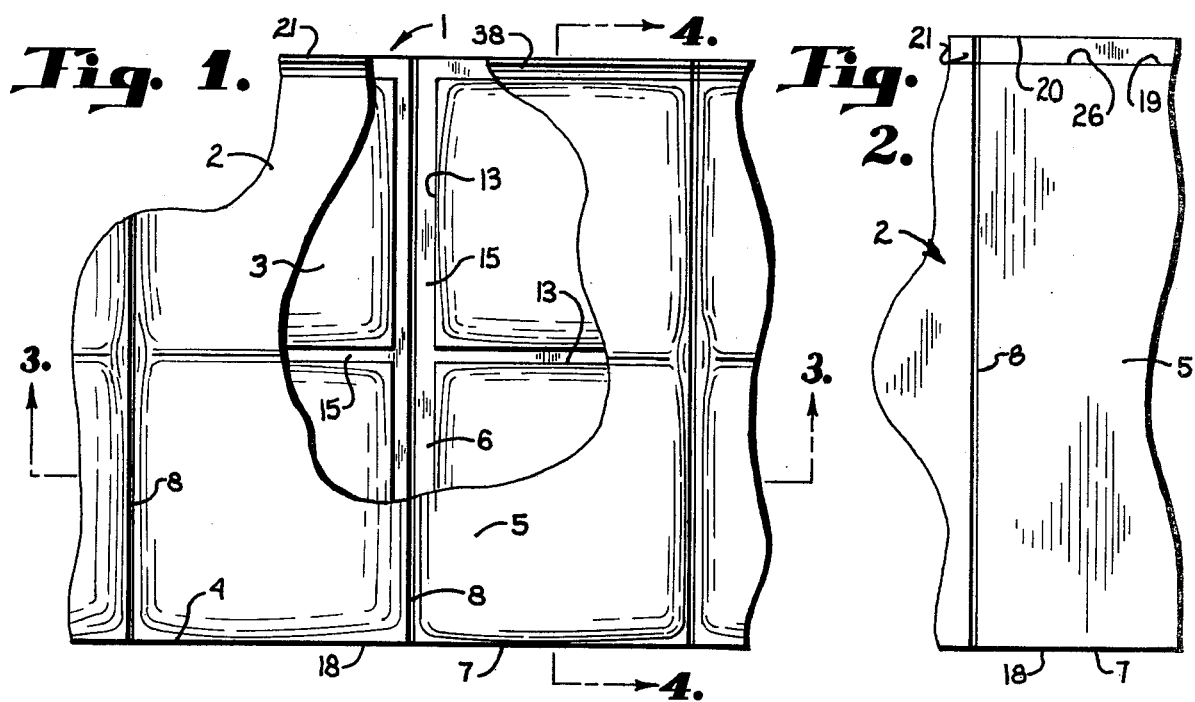
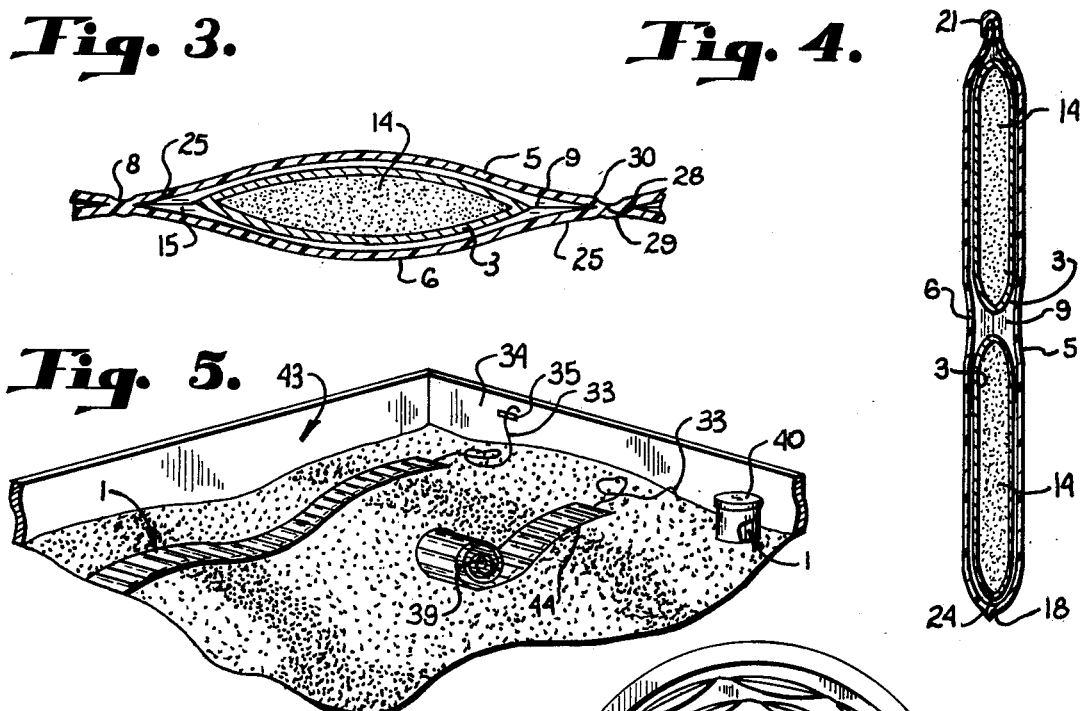
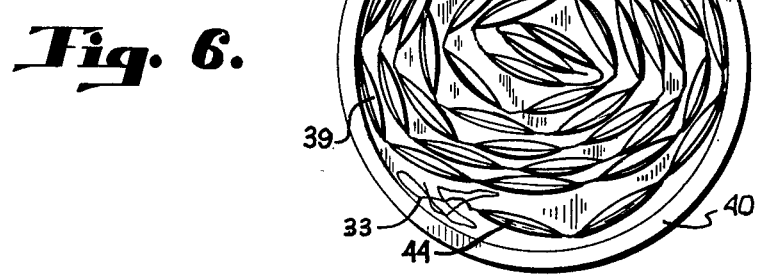

APPARATUS AND METHOD FOR FUMIGATING STORED AGRICULTURAL COMMODITIES

BACKGROUND OF THE INVENTION

This invention relates to fumigants for stored agricultural commodities, and in particular to a fumigation method and applicator for prepackaged pesticides.

Pesticide treatment for stored fodder, grains, and the like is required to prevent infestation of the commodity. Depositories for such commodities, such as silos, elevators, flour mills, warehouses, feed mills, rail cars, barges, and ship holds, typically employ gas emitting pesticides which react with humidity to produce a toxic gas which permeates the stored commodity and completely fumigates same. These fumigants may include gas generating compounds, such as readily decomposable cyanides, alkaline earth phosphides or earth metal phosphides, which react with water vapor in the air contained within the grain depository to produce the toxic gas, which in the last recited examples are hydrogen cyanide, and hydrogen phosphide (phosphine) respectively. These fumigant gases are quite dangerous to humans, and the incomplete reaction of the pesticide with the water vapor leaves a residue of unreacted aluminum phosphide which remains toxic until the reaction is complete.

Certain types of commodities, such as wheat, may be fumigated by preparing the pesticide in a granulated or powdered form, and metering the pesticide directly into the grain as the same is being loaded into the storage depository. However, such a process is limited to special circumstances, and a pesticide residue remains in the wheat because the reaction with the water vapor is not always complete. In order to safeguard the ultimate consumer, regulations have recently been promulgated which require that the residue be is quite fine, the removal process is a very complicated and expensive procedure.

An alternate fumigation method includes the use of an aluminum phosphide chemical in powdered or pellet form, which is prepackaged in measured amounts into porous crepe paper bags or sachets, which when removed from their shipping container and exposed to atmospheric air, will liberate phosphine gas until exhausted or "gassed out". Heretofore, these sachets were manually inserted into the commodity in a uniform fashion after the depository was filled. The bags have been secured to one or more flexible lines by threading the same through an eyelet disposed in one end of the sachet, and tying the line thereto to facilitate removal of the sachets after fumigation. Not only is this method of application quite laborous and time consuming, but can also be quite dangerous, because it exposes the workers to the toxic fumigate gas for an unduly long period of time. The sachets begin to emit gas as soon as they are removed from the airtight shipping container and exposed to the atmosphere. Because the fumigate gases are quite toxic, it is essential that the workers vacate the fumigated areas very quickly before gas concentration levels developed to a hazardous or even lethal level. Hence, the time consuming manual application method used heretofore presents a substantial safety hazard to workmen performing the fumigation. Where very large amounts of grain are to be fumigated, such as in ship holds, a great many sachets must be distributed, therefore requiring a substantial amount of time, and exacerbating the safety hazard to the workmen. The longer the application requires, the longer the workmen are exposed to the hazards associated with the fumigation gas. Consequently, it is of the utmost importance that the application of the sachets to the commodity be performed not only in a uniform and careful manner, but also as quickly as possible.

SUMMARY OF THE INVENTION

The principal objects of the present invention are: to provide an apparatus and method for quickly and safely fumigating large aggregations of a stored commodity; to provide such a method for inexpensively and quickly removing prepackaged pesticide sachets from the stored commodity without adulterating the grain with toxic pesticide residues; to provide such an applicator for quickly and uniformly deploying prepackaged pesticide sachets onto the top surface of the commodity; to provide such an applicator having a plurality of pockets interconnected by flexible hinges for rolling or folding the applicator accordion-style after pesticide gassing to quickly retrieve each and every sachet; to provide such an applicator constructed of a tear resistant, yet porous material; to provide such an applicator constructed of a lightweight, porous material which is non-hygroscopic, to alleviate inadvertent gassing; to provide such an applicator having a flexible line to secure the applicator to the grain despository for positive retrieval of the applicator; to provide such a method wherein the applicator is filled with sachets and retained in an air-tight container to maintain the pesticide in a static state during storage and transport and preserve pesticide strength; to provide such a method wherein the sachets are sealed in the applicator pocket to insure removal of each of the gassed sachets from the commodity; to provide such a method wherein the applicator is rolled into a coil prior to containerization, and unrolled onto the free surface of the commodity; and to provide such an applicator which is economical to manufacture, efficient in use, and particularly well adapted for the proposed use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a side elevational view of an apparatus embodying the present invention and including an applicator with pesticide sachets sealed therein, with portions of the applicator broken away to reveal internal construction.

FIG. 2 is a fragmentary side elevational view of the applicator with an open end thereof unsealed.

FIG. 3 is a cross-sectional view of the sachet filled applicator taken along the line 3—3, FIG. 1.

FIG. 4 is a cross sectional view of the sachet filled applicator taken along the line 4—4, FIG. 1.

FIG. 5 is a partially schematic, perspective view of the applicator shown applied to the surface of a stored agricultural commodity.

FIG. 6 is top plan view of the sachet filled applicator folded into a coil and positioned within a container.

DESCRIPTION OF THE PREFERRED EMBODIMENTS

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

For purposes of description herein, the terms "upper", "lower", "right", "left", "rear", "front", "vertical" and "horizontal", and derivitives thereof, shall relate to the invention as oriented in FIGS. 1 and 5, however, it is to be understood that the invention may assume various alternative orientations, except where expressly specified to the contrary.

The reference numeral 1 generally designates an apparatus for fumigating stored agricultural commodities, such as fodder, wheat, corn, rye, and other types of grains, and includes an applicator 2 for porous envelopes of prepackaged pesticide or sachets 3 of the type which react with moisture in the air and produce a toxic gas. The applicator 2 comprises an elongate strip 4 constructed of a flexible, porous, non-hygroscopic material. The strip has two plies 5 and 6 which are arranged in an overlying relationship and are interconnected along a side edge 7 thereof, and includes a plurality of seams 8 which extend laterally across the strip 4, regularly interconnect the plies 5 and 6, and form pockets 9 shaped for receiving the prepackaged pesticide sachets 3 therein.

The sachets 3 are shaped to directly retain the pesticide chemical therein in either powdered or pellet form, and are constructed of a material which will not react with the pesticide. The illustrated sachets are constructed of a crepe paper, and have a substantially square shape with creased side edges 13 which form a pillow shaped cavity in which the pesticide is retained. In this example, the pesticide 14 is in a powdered form, and two sachets are positioned in each one of the pockets 9. The length and the width of each of the sachets is sized to provide a margin 15 between the side and end edges of the pocket, as well as between adjacent sachets, to facilitate insertion of the two sachets into each pocket.

The applicator plies 5 and 6 are preferably constructed of a single piece of material which is doubled over or folded in approximately half, with a crease 18 formed along the side edge 7. The illustrated strip has free edges 19 and 20 (FIG. 2) positioned opposite the crease 18, and the free edge 20 is spaced slightly apart from the other free edge 19 to form a flap 21 for purposes to be hereinafter described.

Each of the pockets 9 preferably has an elongate shape which is oriented laterally with respect to the longitudinal axis of the strip. The pockets have a length and width in the nature of 8 to 30 centimeters and 3 to 15 centimeters respectively, and are interconnected in very long chains of as much as 300 pockets. Each of the pockets has a closed end 24 disposed at the side edge 7 of the plies, a pair of substantially parallel side edges 25 formed by adjacently disposed seams 8, and an open end 26 located between the free edges 19 and 20 of the plies. The open end 26 of the pocket is shaped to receive one of the sachets 3 therethrough, and is closable with the flap member 21 to retain the sachet in the pocket. The illustrated pockets are of an identical length and width, and receive standard size sachets therein.

The material from which the strip 4 is constructed has negligible water absorption, and very low water vapor retention properties, herein referred to as non-hygroscopic, so as to alleviate inadvertent gassing of the pesticide in the closed storage container. Because the pesticide automatically reacts with moisture and/or water vapor, if the applicator material contains moisture, such as that which might be absorbed from the air prior to forming and assemblying the applicator, when the sachets are inserted into the formed applicator, and the latter is sealed into a container, the moisture in the sachet will react with the pesticide and inadvertently produce fumigant gas in the container. If the amount of container gassing is substantial, the effectiveness of the pesticide is reduced, and it can present a safety hazard to the workers, in so far as when the containers are opened, the workers are exposed directly to an initial discharge of fumigant gas. Because the workers are bending down to open the containers, such fumigant discharges are in close proximity to the mouth and nose of the worker. Further, high concentrations of the fumigant gas are quite volatile and have a tendency to spontaneously combust when the cans are open, thereby creating a fire hazard. In the present invention, the strip material is non-hygroscopic, such as a synethetic fiber, polyolefin, or the like, to alleviate these hazards. A preferred material having very low water retention properties, as well as other advantageous characteristics as discussed hereinafter, is polypropylene.

Although the strip material is non-hygroscopic, the same must also be porous and pervious to water vapor and the fumigant gas, such that when the applicator 2 is positioned over the commodity, water vapor in the air within the depository will infiltrate the applicator, react with the pesticide, and allow the fumigate gas to pass outwardly into the commodity. The preferred material is a lightweight, polypropylene in the shape of a thin, porous sheet having a translucent appearance, with the extrusion direction oriented longitudinally along the material for increased strength in that direction so that the applicator will not break under pulling forces. The polypropylene material has a somewhat wooly or flocculent surface oriented on the interior surfaces of the pocket, and a slicker, more compressed surface oriented on the exterior surfaces of the pockets. The polypropylene material may comprise a sheet of matted, adhered fibers, woven fibers, or blown film, and in the present example, includes extruded longitudinally oriented fibers, with shorter, randomly oriented fibers adhered thereto. The polypropylene material has water vapor absorption/retention capability properties in the nature of less than 1% by weight, and is also tear resistant to alleviate ripping of the applicator which would allow pesticide residue to mix with the commodity. The illustrated film has a thickness in the nature of 0.15 mm, and a density of 20–100 grams per square meter.

Preferably, the plies 5 and 6 are constructed of a heat fusible material, and the seams 8 are heat formed so as to produce a flexible hinge 28 (FIG. 3) between the pockets, along which the plies are integrally connected. In the illustrated example, the polypropylene material has parallel, heat formed seams which are regularly spaced along the entire length of the material, and extend uninterrupted across the material from the crease 18 to the outer free edge 20. The seams may be formed by a straight, heated tool, such as a platen bar, or the like, and in the structure illustrated in FIG. 3, have an integrally molded area 29 of reduced thickness and an opposingly disposed recess or groove 30.

The applicator 2 may be provided with a flexible line 33 (FIG. 5) to aid in the retrieval of the applicator and gassed sachets therein. The line 33 is particularly useful in the fumigation of grains stored for transport such as in barges, ships, rail cars and the like, which generate vibrations and other motions during shipment which tend to bury the sachets in the commodity. One end of the line is attached to an end of the applicator, and the other line end is free and adapted to be attached to a stationary portion 34 of the transport by means such as the illustrated adhesive strip 35.

To assemble the applicator 2, the strip 4 is first folded, with the free edge 19 of the top ply 5 positioned inwardly of the free edge 20 of the bottom ply 6. The strip is then creased along the closed side edge 7, and the heat formed seams 8 are applied regularly along the length of the strip thereby integrally welding the plies 5 and 6 therealong and forming the pockets 9. Two prepackaged sachets 3, each being prefilled with a powdered pesticide 14, are inserted in an end-to-end fashion into each of the pockets 9. The flap 21 is then folded about the edge 19 of the upper ply 5, and means such as a heat formed weld 38 connects the flap with the plies and securely closes the open end of each pocket. The sachet filled applicator is then rolled or folded into a substantially cylindrically shaped coil 39, which is in turn positioned into and sealed within an air-tight container 40 to maintain the pesticide in a static state during storage and transport. The applicator is preferably folded and unfolded with the hinge recesses 30 oriented inwardly.

To fumigate a depository for the agricultural commodity, such as the illustrated ship hold 43, each compartment of the ship hold is first filled to the desired level. The fumigant, still stored and sealed in the containers 40, is transported to the ship hold. The containers 40 are then carefully opened, and the applicator is deployed onto the free surface of the commodity, and positioned into a flat, fully extended position thereover. In the illustrated example, the coil 39 is pulled telescopically from the container 40, and placed with the free end 44 of the coil downwardly, and secured with respect to the commodity. The coil 39 is then rolled out in an unraveling or unfurling manner onto the surface of the commodity. The number of sachets required to properly fumigate the commodity is preselected in accordance with the amount of commodity to be fumigated, and the shape of the depository. If additional fumigant is required, additional filled applicators are deployed onto the surface of the commodity in a similar manner as the first applicator, and the same are arranged in spaced apart rows as illustrated in FIG. 5. Because the sachets are preassembled in the applicator, and the same are arranged in a coil, a great number of sachets may be evenly and uniformly distributed on the surface of the commodity in a very quick and efficient manner by simply rolling out the coil along a substantially straight line on the commodity. The free end of the flexible line 33 may then be attached to a stationary portion of the depository to aid in the retrieval of the pesticide. If the apparatus is being used to fumigate grain fills, the same may be applied by simply securing the free end of the coil with respect to the commodity, such as by attaching the same to the storage container 40, and allowing the coil to roll down the slope side of the grain under gravitational forces. After the applicator has been arranged on the grain, the depository is then closed to form a substantial air-tight structure. The moisture in the air which is captured within the depository infiltrates the applicator 2 and reacts with the pesticide within the sachet, thereby producing a toxic gas which permeates the commodity and fumigates the same. After the sachets have fully gassed, the depository is opened and vented. The gassed sachets are then removed from the commodity by grasping a free end of the applicator, and longitudinally rolling or folding the same accordion-style along the seams until reaching the other end of the applicator. In this manner, each and every one of the sachets is retrieved, without folding or bending the same in a manner which would tend to dispel unreacted pesticide residue from the sachets into the commodity and adulterate the same. The coiled applicator is then removed from the depository and transported to a remote location for disposal.

It is to be understood that while we have illustrated and described certain forms of our invention, it is not to be limited to the specific forms or arrangement of parts herein described and shown.

What we claim and desire to secure by Letters Patent is:

1. An applicator for prepackaged pesticide sachets having a porous envelope with a moisture activated pesticide therein, said applicator comprising:
   (a) an elongate flexible, porous, non-hygroscopic strip of matted adhered fibers having first and second overlying plies interconnected along one side edge thereof; and
   (b) a plurality of seams extending laterally across said plies and interconnecting the same; said seams forming a plurality of pockets therebetween shaped for receiving and retaining the sachets therein; each of said pockets having a closed end disposed at the one side edge of the plies, a pair of substantially parallel side edges formed by adjacently disposed seams, and an open end located at the other side edges of the plies; said pocket open end being shaped to receive one of said sachets therethrough, and closable to retain said sachet in said pocket; each of said seams interconnecting adjacent pockets and forming a flexible hinge therebetween, along which said applicator folds accordion-style for folding up a sachet filled applicator on the surface of an agricultural commodity after pesticide gassing to retrieve said sachets without adulterating the commodity with pesticide residue.

2. An applicator as set forth in claim 1 wherein:
   (a) said first and second plies are each constructed of a heat fusible material; and
   (b) said seams are spaced regularly along the length of the plies and are each heat formed to form said flexible hinge between the pockets and integrally interconnect said plies therealong.

3. An applicator as set forth in claim 2 wherein:
   (a) said first and second plies are each constructed of a polypropylene fibers having low moisture retention to alleviate inadvertent gassing of the sachets.

4. An applicator as set forth in claim 3 wherein:
   (a) said first and second plies include polypropylene fibers oriented generally longitudinally of said strip to prevent breakage under pull loading.

5. An applicator as set forth in claim 3 wherein:

(a) said polypropylene material is of non-woven fibers and includes a smooth exterior surface to facilitate unfolding the applicator onto the surface of the grain and folding the applicator as it is removed from the surface of the grain after pesticide gassing.

6. An applicator as set forth in claim 1 including:
(a) a flexible line having one end thereof attached to a secured end of the applicator, and the other end of the line being spaced for connection with a stationary portion of a depository for the grain to facilitate retrieval of said applicator and sachets therein.

7. An applicator as set forth in claim 2 wherein:
(a) said open end of each of said pockets is sealed closed after insertion of the sachet by a heat formed weld.

8. An applicator as set forth in claim 1 wherein:
(a) said first and second plies are constructed of a single sheet of said material, and the one side edge thereof is folded.

9. A pesticide for in situ fumigation of an agricultural commodity contained in a depository; said pesticide comprising:
(a) a plurality of prepackaged pesticide sachets having a porous envelope with a pesticide therein which reacts with moisture in the air and produces a toxic gas;
(b) an applicator for said sachets including:
  (1) an elongate flexible, porous, heat fusible, non-hygroscopic strip of matted adhered fibers, having first and second overlying piles interconnected along one side edge thereof;
  (2) a plurality of heat formed seams extending laterally across said overlying plies, being spaced regularly along the length thereof, and integrally interconnecting said plies along said seams; said seams forming a plurality of pockets therebetween in which said sachets are received and retained; each said pockets having a closed end disposed at the one side edge of the plies, a pair of substantially parallel side edges formed by adjacently disposed seams, and an open end located at the other side edge of the plies; said pocket open end being shaped to receive one of said sachets therethrough, and being closable to retain said sachet in said pocket; said seams interconnecting adjacent pockets and forming a flexible hinge therebetween along which said applicator folds accordion-style for folding up a sachet filled applicator into a coil; and
(c) a substantially airtight container surrounding and retaining said coil for maintaining said pesticide in a static state during storage and transport of the pesticide and preserving pesticide strength.

10. A pesticide as set forth in claim 9 wherein:
(a) said first and second plies are each constructed of polypropylene fibers, and said plies have water vapor absorption/retention capabilities in the nature of less than 1% by weight; and
(b) said open end of each of said pockets is sealed closed after insertion of the sachet by a heat formed weld.

11. A method for in situ fumigation of an agricultural commodity contained in a closable depository; said method comprising the steps of:
(a) providing a plurality of prepackaged pesticide sachets of the type which react with moisture in the air and produce a toxic gas;
(b) providing an elongate applicator characterized by being formed of a flexible, porous, non-hygroscopic strip of matted, adhered, heat fusible fibers, said applicator having a plurality of laterally extending pockets, each being hingedly interconnected along a seam and shaped for receiving a sachet therein;
(c) inserting a sachet into each of said pockets;
(d) deploying the filled applicator onto the free surface of the commodity, and positioning the applicator into a flat and fully extended position thereover;
(e) closing said depository to form a substantially airtight structure;
(f) reacting the pesticide with moisture in the air, whereby the toxic gas produced permeates the commodity and fumigates the same;
(g) venting said toxic gas from said depository, and then opening said depository;
(h) grasping a free end of said applicator and longitudinally folding the same accordion-style along the seams into a coil so as to quickly retrieve each of the sachets without adulterating the commodity with pesticide residue; and
(i) removing said coil from the depository and transporting the same to a remote location for disposal.

12. A method as set forth in claim 11 including:
(a) securing one end of said applicator to a stationary portion of said commodity depository to facilitate removal.

13. A method as set forth in claim 11 including:
(a) folding said applicator into a coil after inserting the sachets into the applicator pockets; and
(b) placing said coil into an airtight storage container and sealing the same closed for maintaining said pesticide in a static state during storage and transport for preserving pesticide strength.

14. A method as set forth in claim 13 wherein:
(a) said filled applicator is deployed by removing said coil from said container, and quickly unfolding the same out onto the surface of the commodity to reduce human exposure to the gas and to provide safe fumigation of the commodity.

15. A method as set forth in claim 11 including:
(a) providing a plurality of filled applicators, and deploying the same in spaced apart rows on the surface of the commodity.

* * * * *